United States Patent
Frey et al.

(10) Patent No.: US 10,337,502 B2
(45) Date of Patent: Jul. 2, 2019

(54) EARLY DETECTION OF WIND TURBINE DEGRADATION USING ACOUSTICAL MONITORING

(71) Applicant: Inventus Holdings, LLC, Juno Beach, FL (US)

(72) Inventors: Ann Frey, Port Saint Lucie, FL (US); Frank Roark, Boca Raton, FL (US); Miguel Gonzalez, Jupiter, FL (US); Daniel M. Brake, Hobe Sound, FL (US)

(73) Assignee: Inventus Holdings, LLC, Juno Beach, FL (US)

( * ) Notice: Subject to any disclaimer, the term of this patent is extended or adjusted under 35 U.S.C. 154(b) by 342 days.

(21) Appl. No.: 15/443,883

(22) Filed: Feb. 27, 2017

(65) Prior Publication Data

US 2017/0167471 A1    Jun. 15, 2017

Related U.S. Application Data

(63) Continuation of application No. 14/077,327, filed on Nov. 12, 2013, now Pat. No. 9,581,141.

(60) Provisional application No. 61/725,743, filed on Nov. 13, 2012.

(51) Int. Cl.
| | |
|---|---|
| *F03D 17/00* | (2016.01) |
| *G01N 29/14* | (2006.01) |
| *G01N 29/42* | (2006.01) |
| *G01N 29/44* | (2006.01) |
| *G05B 13/02* | (2006.01) |

(52) U.S. Cl.
CPC .............. *F03D 17/00* (2016.05); *G01N 29/14* (2013.01); *G01N 29/42* (2013.01); *G01N 29/4427* (2013.01); *G05B 13/021* (2013.01); *F05B 2260/80* (2013.01); *F05B 2270/333* (2013.01); *F05B 2270/335* (2013.01); *G01N 2291/2693* (2013.01); *Y02E 10/722* (2013.01)

(58) Field of Classification Search
CPC ........ F03D 17/00; G01N 29/14; G01N 29/42; G01N 29/4427; G01N 2291/2693; G05B 13/021; F05B 2260/80; F05B 2270/333; Y02E 10/722
See application file for complete search history.

(56) References Cited

U.S. PATENT DOCUMENTS

| | | |
|---|---|---|
| 2009/0169378 A1 | 7/2009 | Menke |
| 2011/0135442 A1 | 6/2011 | Kerber |
| 2012/0166000 A1 | 6/2012 | Ellena et al. |

FOREIGN PATENT DOCUMENTS

JP          2007192828         8/2007

*Primary Examiner* — Igor Kershteyn
(74) *Attorney, Agent, or Firm* — Jeffrey N. Giunta; Fleit Gibbons Gutman Bongini & Bianco. P.L.

(57) ABSTRACT

Disclosed is a system and method for monitoring wind turbines, generally comprising: measuring sound levels of a plurality of wind turbines; checking the sound levels of each of the plurality of wind turbines against sound levels of others of the plurality of wind turbines; detecting that one of the plurality of wind turbines is an anomalous wind turbine based upon the checking; and generating a corrective action alarm signal identifying the anomalous wind turbine based upon the detecting.

20 Claims, 4 Drawing Sheets

EARLY DETECTION OF WIND TURBINE DEGRADATION USING ACOUSTICAL MONITORING

FIELD OF THE DISCLOSURE

The present invention relates to a system and method for monitoring wind turbines. More particularly, the present invention relates to a system and method for detection of wind turbine degradation using acoustical monitoring.

BACKGROUND

Recently, wind turbines have received increased attention as an environmentally safe and relatively inexpensive alternative energy source. With this growing interest, considerable efforts have been made to develop wind turbines that are reliable and efficient.

Generally, a wind turbine includes a rotor having a rotatable hub assembly having multiple rotor blades. The rotor is mounted within a housing or nacelle, which is positioned on top of a truss or tubular tower. Utility grade wind turbines (i.e., wind turbines designed to provide electrical power to a utility grid) can have large rotors (e.g., 30 or more meters in diameter). Blades on these rotors transform wind energy into a rotational torque or force that drives one or more generators. The generators may be rotationally coupled to the rotor through a gearbox. The gearbox steps up the inherently low rotational speed of the turbine rotor for the generator to efficiently convert mechanical energy to electrical energy, which is fed into a utility grid.

Gearless direct drive wind turbines also exist. The rotor, generator, gearbox and other components are typically mounted within a housing, or nacelle, that is positioned on top of a tower.

Wind turbine components, such as bearings, gears, and/or rotor blades may become worn down or damaged over time. To detect such component damage, wind turbines often include a monitoring system that measures vibrations generated by the component during an operation of the wind turbine. Such monitoring systems may be complex and/or may require significant computational resources to extract component damage information from the measured vibrations.

Operational detriments may eventually cause suboptimal performance, whether temporarily (e.g., rotor blade icing) or indefinitely (e.g., structural damage to a rotor blade). At least some known methods of monitoring wind turbines detect operational detriments indirectly by detecting anomalies or symptoms, such as decreased power output and/or inoperability, of a wind turbine. Moreover, because many potential causes exist for such anomalies or symptoms, determining the root cause of an anomaly or symptom requires manual inspection by a service technician, introducing undesirable delay and expense before the root cause can be addressed. In view of the disadvantages associated with the current solutions, there is a need in the art for improved methods and systems for monitoring wind turbines.

DETAILED DESCRIPTION

Figure 1:
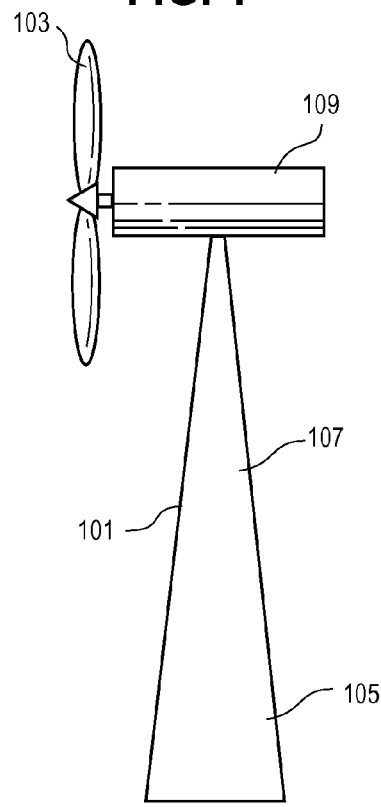
FIG. 1 illustrates a wind turbine having a tower base, middle section, and nacelle.

The following detailed description and the appended drawings describe and illustrate some embodiments of the invention for the purpose of enabling one of ordinary skill in the relevant art to make and use the invention. As such, the detailed description and illustration of these embodiments are purely illustrative in nature and are in no way intended to limit the scope of the invention, or its protection, in any manner. It should also be understood that the drawings are not to scale and in certain instances details have been omitted, which are not necessary for an understanding of the present invention, such as details of fabrication and assembly.

In accordance with one embodiment, a wind sound detection unit may include a microphone, a filter, a processor, and a communications module. Those elements may be integrated in a small enclosure. The detection unit may be mounted on different locations on the turbine which have access to a turbine communications network. In one embodiment, the wind sound detection unit may be placed on a lower section of a tower supporting the wind turbine if the turbine does not have network connectivity in the nacelle, for example. In one embodiment, the detection unit may be installed in the nacelle.

Through use of the microphone, the detection unit may detect acoustic emissions generated by the turbine. The acoustic emissions are filtered and processed by a processor to generate sound level data. The sound level data may be communicated using a communications module over a turbine network to a software program on a SCADA server or a dedicated PLC. The wind sound analysis may be done either in the detection unit or in a program in the SCADA server or in a dedicated PLC. The term "monitoring device" is used herein to refer to the PLC, SCADA, or any other monitoring device that runs the monitoring software.

A Modbus interface may also be used to configure the detection unit. Exemplary configuration parameters may include:

Network address.

Alarm levels of the frequency ranges, e.g., 20 frequency range alarm limits (the absolute minimum and maximum frequencies may be determined by the sensitivity of the selected microphone).

Configuring the system so that the Modbus IP communications interface is polled periodically (e.g., every 10 seconds) during operation, with the polled data including maximum sound level for each of the frequency ranges.

Resetting the maximum sound level to zero after each read or poll.

Setting the length of sound capture files (e.g., in seconds).

Calibration of the sound levels to compensate for variations in microphone sensitivity.

The configuration parameter related to resetting of maximum sound or volume level to zero is further explained. In one embodiment, to detect a maximum volume within a polling period, each poll resets all the detected maximum sound levels to zero.

In another embodiment, the length of sound capture files is configured. For example, the system may allow for real-time sound file creation by the detection unit. These captures will collect the microphone input to a WAV file for remote analysis.

In one embodiment, the wind sound detection unit may include a single circuit board mounted in a small enclosure. The circuit board may have the microphone mounted on it or the microphone may be mounted externally to the detection unit. The circuit board may also include a processor, a filtering device (for example, a digital signal processor ("DSP")), and the communications module (for example, an Ethernet connection interface). In one embodiment, by using the Modbus protocol as a communications standard, data collection and analysis may be implemented in a variety of ways. For example, sound analysis may be performed by software in the detection unit or a SCADA server or by a dedicated PLC connected to both the turbine network (for example, a LAN) and a control network (for example, a WAN). In another embodiment, sound analysis may be performed at the detection unit.

As illustrated in FIG. 1, one embodiment of the monitoring system of the present invention includes a tower 101 for supporting the wind turbine 103 and three wind sound detection units installed on a plurality of testing points (for collecting the sound samples). As illustrated in FIG. 1, testing points may be located on the tower base 105, a tower middle section 107, and the nacelle 109.

Figure 2:
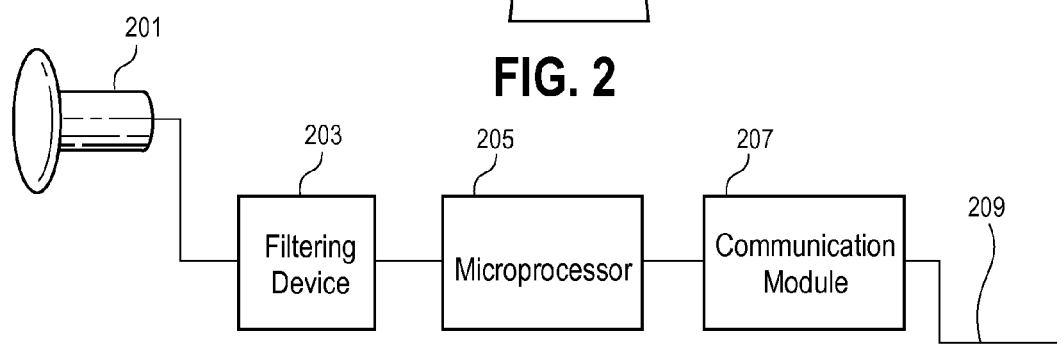
FIG. 2 illustrates a detection unit used in accordance with one embodiment.

As illustrated in FIG. 2, the wind sound detection unit may include a microphone 201, a filtering device 203, a processor 205, and a communications module 207 such as an Ethernet connection interface. In one embodiment, the filtering device 203, microprocessor 205, communications module 207, and/or the microphone 201 may be supplied with power and may exchange data through use of Power Over Ethernet ("POE") technology 209. In one embodiment, the filtering device 203 may be programmed to split the signal detected by the microphone 201 into a plurality of signals in accordance with different frequency bands, each of which will have a predetermined frequency range.

Figure 3:
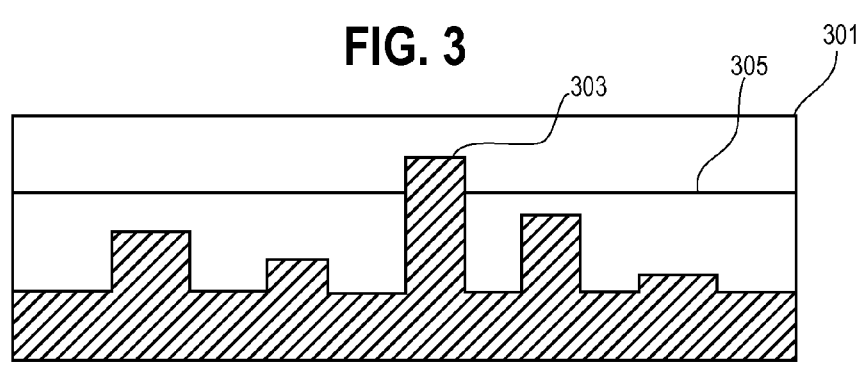
FIG. 3 illustrates a display of sound or noise levels detected at different frequency bands as well as a single sound or noise threshold for all frequency bands of interest in accordance with one embodiment.

As illustrated in FIG. 3, one embodiment also includes a display 301 of sound or noise levels detected at different frequency bands as well as a single sound or noise threshold for all frequency bands of interest. In the figure, noise or sound detected in one frequency band 303 exceeds the single sound threshold 305, which in one embodiment results in the generation of an alarm signal. In other embodiments of the invention, each frequency band may have an associated threshold which may vary or may be set depending on the frequency band.

Figure 4:
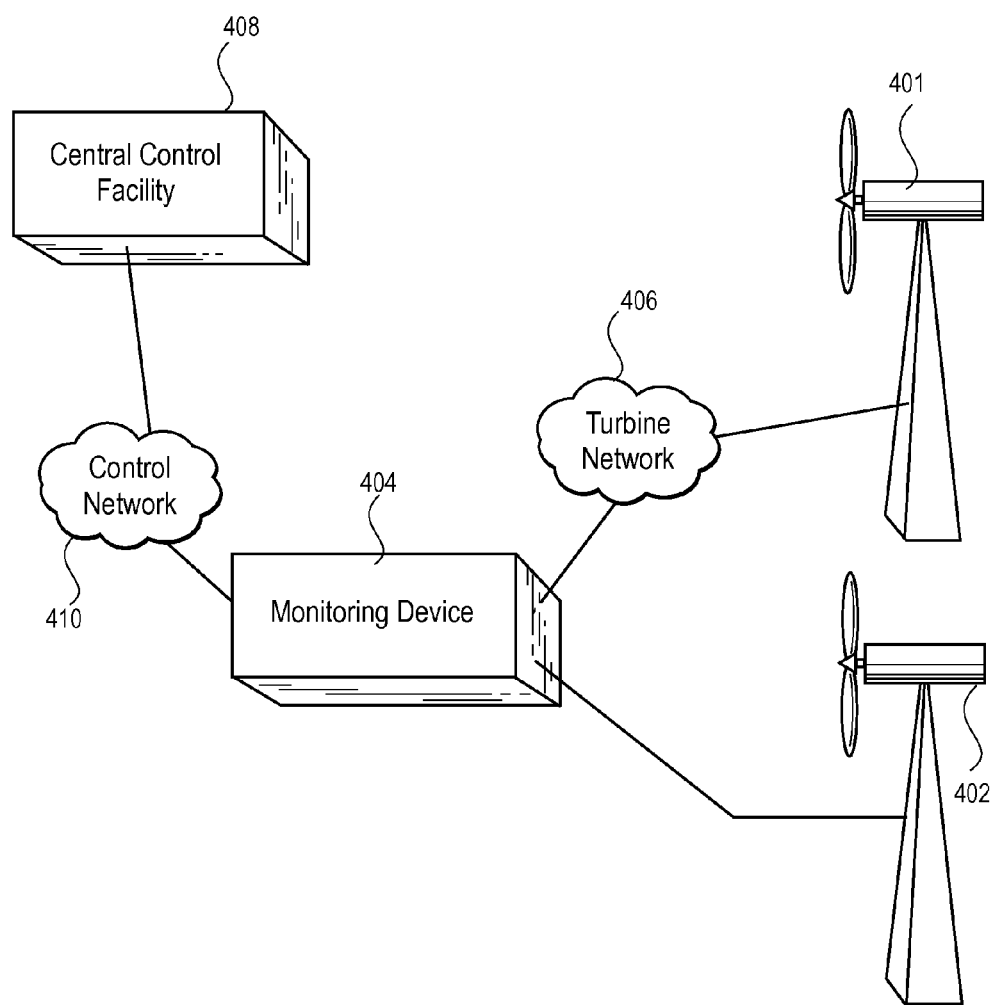
FIG. 4 illustrates a system for acoustical monitoring of wind turbines in accordance with one embodiment.

FIG. 4 illustrates a high level description of a monitoring system in accordance with one embodiment. The figure illustrates two different wind turbines, 401 and 402, in a wind farm, each turbine having two or more wind sound detection units. As illustrated, data may be exchanged between the detection units and a monitoring device 404 (for example, SCADA or PLC) over a turbine network 406 (for example, a LAN). As further depicted in FIG. 4, data is also exchanged between the monitoring device 404 and a central control facility 408 over a control network 410 (for example, a WAN). In one embodiment, the central control facility 408 sends commands to the monitoring device 404 to take corrective actions with respect to the operation of a wind turbine upon receipt of an alarm signal.

Figure 5:
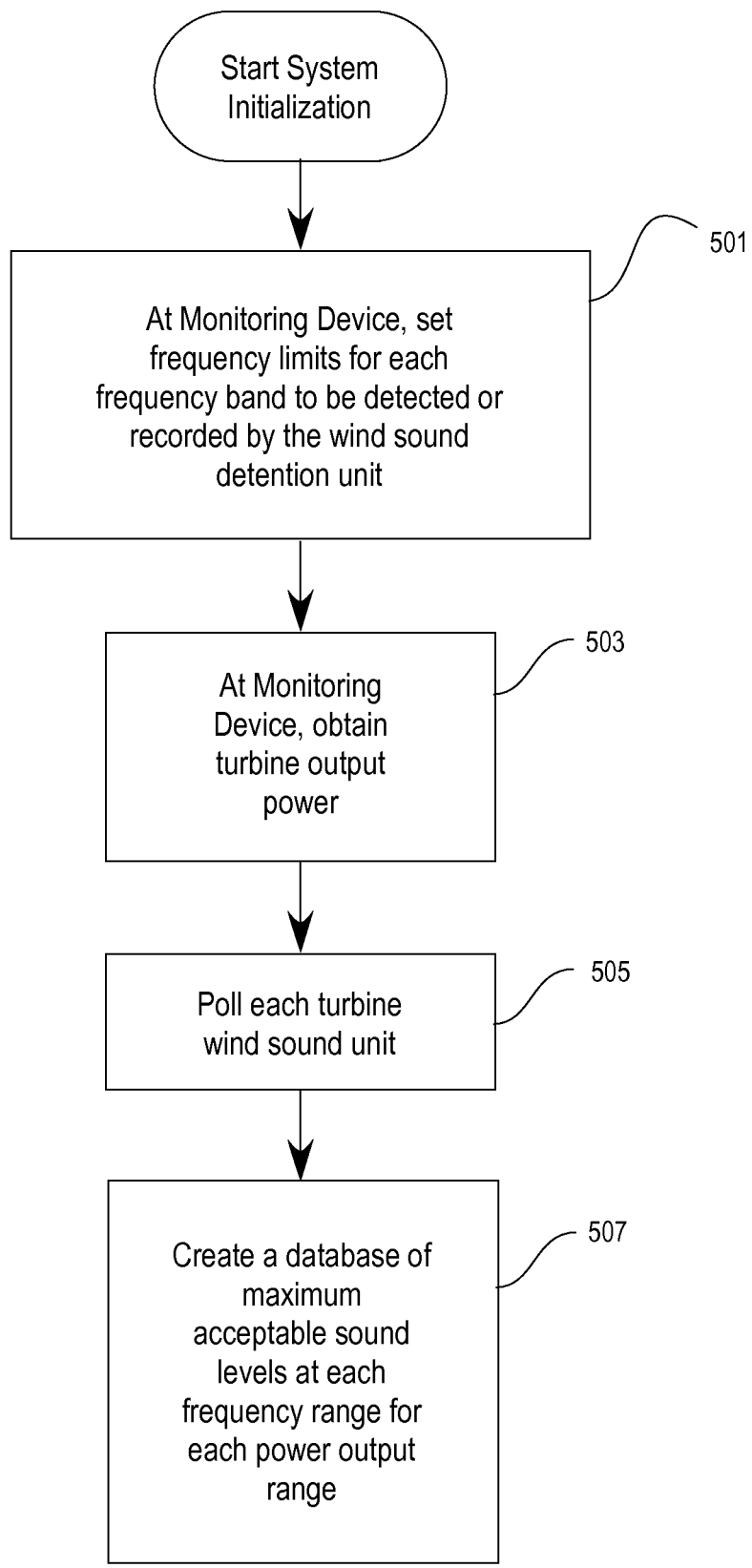
FIG. 5 illustrates a flowchart describing an initialization phase for a method for acoustical monitoring of wind turbines in accordance with one embodiment.

In accordance with illustrative embodiments, the sound analysis may be performed by software in the detection unit or in the SCADA server or by a dedicated PLC in two phases: 1) an initialization phase where the software learns what the normal sound levels are, or where the normal sound levels are determined for each of the frequency ranges and the alarm levels are preloaded into the detection units; and 2) an operation phase, where the turbines are monitored for variances from that normal level. For example, as illustrated in FIG. 5, at the initialization stage the software program run by the monitoring device may implement the following tasks:

Set the bandwidth for each of the frequency bands in the wind sound detection unit (step 501).

Obtain the turbine real time power output from the SCADA system (step 503).

Poll each turbine wind sound detection unit (step 505).

Create a database of maximum sound levels at each frequency range for each power output range, for example, at 50 kW resolution (step 507).

The creation of a database of maximum sound levels at each frequency range for each power output range is further explained. The expected sound levels may change depending on the turbine output power. A turbine at full generation is expected to emit more noise than a turbine at low generation. Thus, the system of the present invention may read the maximum sound levels generated in ranges of power generation with a 50 kW resolution. For example the system may read a first maximum sound level at a range of 0-50 kW; a second maximum sound level at a range of 51-100 kW; and a third maximum sound level at a range of 101-150 kW, and so on.

Figure 6:
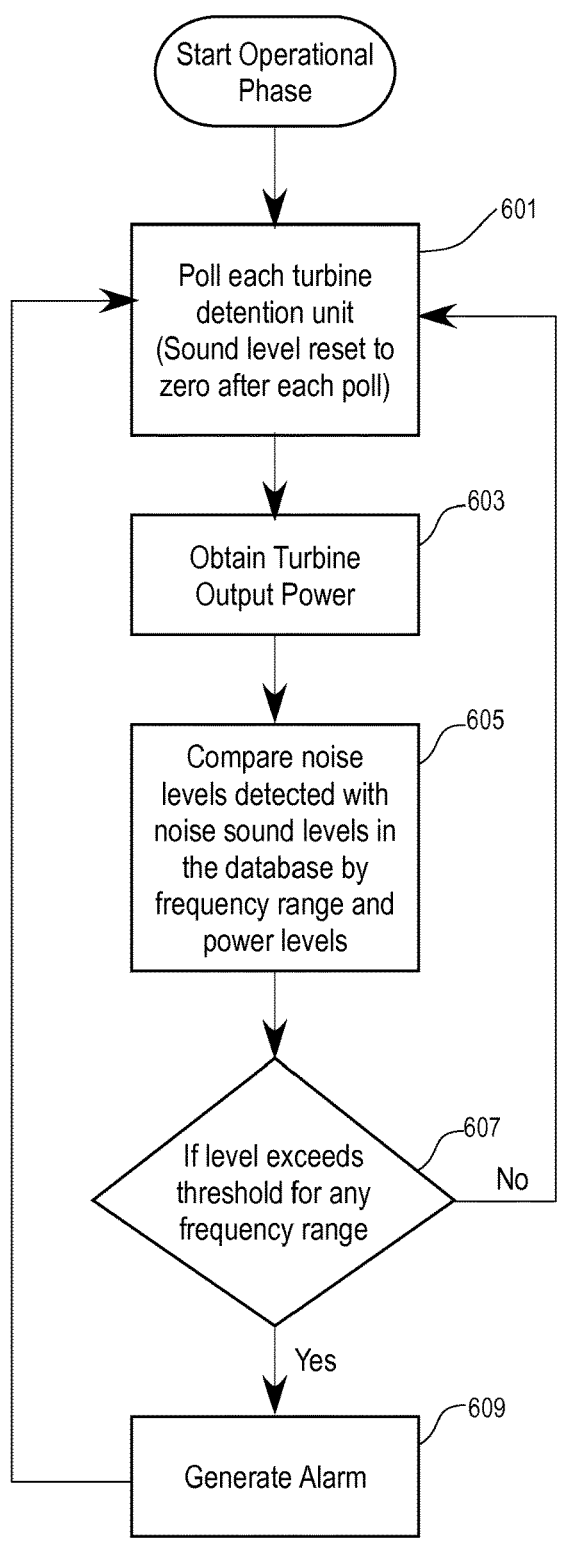
FIG. 6 illustrates a flowchart describing an operational phase for a method for acoustical monitoring of wind turbines in accordance with one embodiment.

At the conclusion of the initialization phase, the measured sound levels of each of the turbines may be checked against the others (of the same type of turbine) to detect any anomalous turbines. As illustrated in FIG. 6, in one embodiment, after completion of the initialization phase the software may be set to an operational phase to perform the following tasks:

Poll each turbine (e.g., all turbines in a wind farm or a subset thereof) wind sound detection unit every 10 seconds (step 601).

Obtain the turbine power output from the SCADA system (step 603).

Compare current noise levels against the noise or sound levels stored in a database by frequency and note any change from normal levels (step 605). This provides the ability to compare normal and abnormal readings for similar turbines across the fleet. The database may exist anywhere on the network, for example, at each turbine site or remotely.

Determine if noise level exceeded its normal sound levels for a defined period of time (step 607).

Generate alarms after a turbine has exceeded its normal sound levels for a defined period of time (step 609). For example, the alarm may go off if a single frequency band exceeds expected levels. A person of ordinary skill in the art would recognize that some types of failures will occur in a specific frequency range.

In one embodiment, the detection unit determines the frequency ranges associated with an alarm. Thus, instead of merely forwarding sound data to a PLC or SCADA, the detection units may perform the sound threshold comparisons.

In another embodiment, a WAV file is captured directly by the detection unit so that sound files are created in the detection unit, as opposed to having the detection units forward sound samples to the SCADA or PLC.

The present description of the invention makes reference to the use of SCADA systems and PLCs for monitoring and controlling the operation of wind turbines. In general, use of SCADA systems and PLCs to monitor wind turbines is known in the art. The present application incorporates by reference U.S. patent application Ser. No. 12/979,752 entitled "REMOTE WIND TURBINE RESET SYSTEM AND METHOD." That application, incorporated herein by reference in its entirety, discloses the use of programmable logic controllers ("PLCs") and Supervisory Control and Data Acquisition ("SCADA") systems to monitor and control wind turbines.

The descriptions set forth above are meant to be illustrative and not limiting. Various modifications of the invention, in addition to those described herein, will be apparent to those skilled in the art from the foregoing description. Such modifications are also intended to fall within the scope of the concepts described herein.

The foregoing description of possible implementations consistent with the present invention does not represent a comprehensive list of all such implementations or all variations of the implementations described. The description of only some implementation should not be construed as an intent to exclude other implementations. For example, artisans will understand how to implement the invention in many other ways, using equivalents and alternatives that do not depart from the scope of the invention. Moreover, unless indicated to the contrary in the preceding description, none of the components described in the implementations are essential to the invention.

The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods.

What is claimed is:

1. A method comprising:
   measuring sound levels of a plurality of wind turbines;
   checking the sound levels of each of the plurality of wind turbines against sound levels of others of the plurality of wind turbines;
   detecting that one of the plurality of wind turbines is an anomalous wind turbine based upon the checking; and
   generating a corrective action alarm signal identifying the anomalous wind turbine based upon the detecting.

2. The method according to claim 1 wherein a subset of the plurality of wind turbines are of a same type and the checking only compares sound levels against sound levels of the same type of wind turbine.

3. The method according to claim 1 wherein the plurality of wind turbines are included within a wind farm.

4. The method according to claim 3 wherein the wind farm includes different wind turbines and a subset of the plurality of wind turbines are of a same type, and
   the checking only compares sound levels against sound levels of the same type of wind turbine within the wind farm.

5. The method according to claim 4 wherein the checking is based on an initial measurement of sound levels, and the method further comprises:
   generating a database of acceptable sound levels based upon the initial measurement;
   polling each of the plurality of wind turbines to measure corresponding measured sound levels;
   comparing the corresponding measured sound levels from the polling with the database of acceptable sound levels; and
   generating a subsequent corrective action signal based upon the comparing.

6. The method according to claim 1 wherein the measuring comprises measuring an initial measurement of sound levels, and the method further comprises:
   generating a database of acceptable sound levels based upon the initial measurement;
   polling each of the plurality of wind turbines to measure a respective corresponding measured sound level for each wind turbine;
   comparing the respective corresponding measured sound level from the polling with the database of acceptable sound levels; and
   generating a subsequent corrective action signal based upon the comparing.

7. The method according to claim 6 wherein
   the measuring measures respective initial measurement sound levels in a plurality of frequency ranges, the generating a database generates the database of acceptable sound levels for each of the plurality of frequency ranges based upon the initial measurement sound levels,
   the polling further measures respective measured sound levels in the plurality of frequency ranges, and
   the comparing compares the respective measured sound levels in the plurality of frequency ranges from the polling against the acceptable sound levels for each of the plurality of frequency ranges stored in the database of acceptable sound levels.

8. The method according to claim 6 further comprising
   obtaining an initial power output of the plurality of wind turbines associated with the measuring the initial measurement of sound levels, wherein
   the measuring the initial measurement of sound levels further measures a respective initial measurement of sound level associated with each initial power output within a plurality of power levels,
   the generating further generates the database comprising acceptable sound levels for each of the plurality of power levels based upon the measuring the initial measurement of sound levels,
   the polling further obtains current power output levels for each of the plurality of wind turbines associated with the respective measured sound level for each wind turbine, and
   the comparing further compares the respective measured sound level for each wind turbine with acceptable sound levels associated with the current power output levels stored in the database.

9. The method according to claim 8, wherein the plurality of wind turbines are included within a wind farm including different wind turbines,
- a subset of the plurality of wind turbines are of a same type, and
- the comparing only compares sound levels of the same type of wind turbine within the wind farm,
- wherein the measuring measures respective initial measurement sound levels in a plurality of frequency ranges,
- the generating a database generates the database of acceptable sound levels for each of the plurality of frequency ranges and for each of the plurality of power levels based upon the initial measurement,
- the polling further measures respective measured sound levels in the plurality of frequency ranges, and
- the comparing further compares the respective measured sound levels in the plurality of frequency ranges from the polling with the acceptable sound levels associated with the current power output levels stored in the database of acceptable sound levels.

10. A system comprising:
- a sound detection unit configured to measure sound levels of a plurality of wind turbines;
- a sound analyzer configured to:
  - check the sound levels of each of the plurality of wind turbines against sound levels of others of the plurality of wind turbines;
  - detect that one of the plurality of wind turbines is an anomalous wind turbine based upon the check of the sound levels; and
  - generate a corrective action alarm signal identifying the anomalous wind turbine based upon a detection that one of the plurality of wind turbines is an anomalous wind turbine.

11. The system according to claim 10 wherein a subset of the plurality of wind turbines are of a same type and the sound analyzer is configured to check by at least comparing sound levels against sound levels of the same type of wind turbine.

12. The system according to claim 10 wherein the plurality of wind turbines are included within a wind farm.

13. The system according to claim 12 wherein the wind farm includes different wind turbines and a subset of the plurality of wind turbines are of a same type, and
- the sound analyzer is configured to check by at least comparing sound levels against sound levels of the same type of wind turbine within the wind farm.

14. The system according to claim 13 wherein the sound analyzer is configured to check based on an initial measurement of sound levels, and the sound analyzer is further configured to:
- generate a database of acceptable sound levels based upon the initial measurement;
- poll each of the plurality of wind turbines to measure corresponding measured sound levels;
- compare the respective corresponding measured sound level from the polling with the database of acceptable sound levels; and
- generate a subsequent corrective action signal based upon the comparing.

15. The system according to claim 10 wherein the sound detection unit is configured to at least measure an initial measurement of sound levels, and the sound analyzer is further configured to:
- generate a database comprising a database of acceptable sound levels based upon the initial measurement;
- poll by at least polling each of the plurality of wind turbines to measure a respective corresponding measured sound level for each wind turbine;
- compare the respective corresponding measured sound level from the poll with the database of acceptable sound levels; and
- generate a subsequent corrective action signal based upon a comparison of the respective measured sound level with the database.

16. The system according to claim 15, wherein the sound analyzer is further configured to:
- measure respective initial measurement sound levels in a plurality of frequency ranges,
- generate the database by generating a database of acceptable sound levels for each of the plurality of frequency ranges based upon the initial measurement,
- poll by at least further measuring respective measured sound levels in the plurality of frequency ranges, and
- compare by at least comparing the respective measured sound level in the plurality of frequency ranges from the poll against the acceptable sound levels for each of the plurality of frequency ranges stored in the database of acceptable sound levels.

17. The system according to claim 15, wherein the sound analyzer is further configured to:
- obtain an initial power output of the plurality of wind turbines associated with the initial measurement of sound levels;
- measure the initial measurement of sound levels by at least further measuring a respective initial measurement of sound level associated with each initial power output within a plurality of power levels;
- generate the database comprising acceptable sound levels for each of the plurality of power levels based upon the measuring the initial measurement of sound levels;
- poll by at least further obtaining current power output levels for each of the plurality of wind turbines associated with the respective measured sound level for each wind turbine; and
- compare by at least further comparing the respective corresponding measured sound level for each wind turbine with acceptable sound levels associated with the current power output levels sored in the database.

18. The system according to claim 17,
- wherein the plurality of wind turbines are included within a wind farm including different wind turbines,
- a subset of the plurality of wind turbines are of a same type, and
- wherein the sound analyzer is further configured to:
  - compare by only comparing sound levels of the same type of wind turbine within the wind farm;
  - measure sound levels by at least measuring respective initial measurement sound levels in a plurality of frequency ranges;
  - generate a database by at least generating a database of acceptable sound levels for each of the plurality of frequency ranges and for each of the plurality of power levels based upon the initial measurement;
  - poll by at least further measuring respective measured sound levels in the plurality of frequency ranges; and
  - compare by at least further comparing the respective measured sound level in the plurality of frequency ranges from the poll with the acceptable sound levels associated with the current power output levels stored in the database of acceptable sound levels.

19. A method for monitoring a wind turbine having one or more detection units, each said detection unit comprising a microphone for picking up acoustic emissions from said wind turbine and outputting a signal corresponding to said acoustic emissions, and a processor for processing said signal and generating sound level data, said method comprising:

polling said wind turbine at repeating time intervals;

obtaining a real time power output range for said wind turbine from a SCADA server or programmable logic controller in communication with said detection unit;

comparing a sound level detected by said detection unit against a sound level stored in a database;

determining if said sound level detected by said detection unit exceeded a normal sound level corresponding to a real time power output level of said wind turbine for a defined period of time; and generating alarms if said sound level detected by said detection unit exceeds said normal sound level.

20. The method of claim 19, further comprising:

splitting said signal into a plurality of signals according to a plurality of frequency bands; and processing said plurality of signals and generating sound level data-corresponding to at least a subset of said plurality of frequency bands, wherein the comparing comprises comparing a sound level detected by said detection unit against a sound level stored in a database by frequency.

\* \* \* \* \*